(12) United States Patent
Vakili et al.

(10) Patent No.: US 12,599,567 B2
(45) Date of Patent: Apr. 14, 2026

(54) METHOD FOR PREPARING A VETERINARY MEDICAMENT DOSAGE WITH INKS AND A VETERINARY MEDICAMENT DOSAGE OBTAINABLE BY THE METHOD

(71) Applicant: CURIFYLABS OY, Helsinki (FI)

(72) Inventors: Hossein Vakili, Turku (FI); Sari Airaksinen, Helsinki (FI)

(73) Assignee: CurifyLabs Oy, Helsinki (FI)

( * ) Notice: Subject to any disclaimer, the term of this patent is extended or adjusted under 35 U.S.C. 154(b) by 71 days.

(21) Appl. No.: 18/712,370

(22) PCT Filed: Jun. 13, 2022

(86) PCT No.: PCT/FI2022/050406
§ 371 (c)(1),
(2) Date: May 22, 2024

(87) PCT Pub. No.: WO2023/094722
PCT Pub. Date: Jun. 1, 2023

(65) Prior Publication Data
US 2024/0415776 A1      Dec. 19, 2024

(30) Foreign Application Priority Data
Nov. 29, 2021    (FI) ..................................... 20216215

(51) Int. Cl.
*A61K 9/28* (2006.01)
*A61K 45/06* (2006.01)
*B33Y 10/00* (2015.01)

(52) U.S. Cl.
CPC .......... *A61K 9/2893* (2013.01); *A61K 9/2866* (2013.01); *A61K 45/06* (2013.01); *B33Y 10/00* (2014.12)

(58) Field of Classification Search
None
See application file for complete search history.

(56) References Cited

U.S. PATENT DOCUMENTS 7,348,027 B2    3/2008   Rose et al.
9,844,930 B2    12/2017  Hoover et al.
(Continued)

FOREIGN PATENT DOCUMENTS

EP        2532349 A1    12/2012
EP        1996029 B1    9/2015
(Continued)

OTHER PUBLICATIONS

Sjöholm et al.; 3D-Printed Veterinary Dosage Forms—a Comparative Study of Three Semi-Solid Extrusion 3D Printers; Pharmaceutics 2020, 12, 1239.*
Ehtezazi et al.; The Application of 3D Printing in the Formulation of Multilayered Fast Dissolving Oral Films; Journal of Pharmaceutical Sciences, 107, (2018), 1076-1085.*
Touraj Ehtezazi, et al., "The Application of 3D Printing in the Formulation of Multilayered Fast Dissolving Oral Films", Journal of Pharmaceutical Sciences, vol. 107, No. 4, Apr. 1, 2018, pp. 1076-1085 (10 pages).
(Continued)

*Primary Examiner* — Michael P. Rodriguez
(74) *Attorney, Agent, or Firm* — Laine IP Oy

(57) ABSTRACT
The present disclosure relates to a method for preparing a veterinary medicament dosage using a 3D printer. The method comprises printing a plurality of layers comprising one or more active pharmaceutical ingredients (APIs) on the printing substrate, so that each layer comprising API is surrounded by layers comprising one or more taste masking agents, until a required dose of the one or more APIs is obtained. The disclosure also relates to a veterinary medicament dosage obtainable by the method.

15 Claims, 1 Drawing Sheet

(56)     References Cited

U.S. PATENT DOCUMENTS

2008/0026040 A1      1/2008  Farr et al.
2020/0016092 A1*     1/2020  Bernardo ............. A61K 9/0056
2022/0249393 A1*     8/2022  Daud ................... A61K 9/7007

FOREIGN PATENT DOCUMENTS

EP          1562549 B1     3/2017
EP          2755498 B1     2/2018
EP          3789015 A1     3/2021
WO       2019025857 A2     2/2019
WO       2019199505 A1    10/2019
WO       2020035680 A1     2/2020

OTHER PUBLICATIONS

Erica Sjoholm, et al., "3D-Printed Veterinary Dosage Forms—a Comparative Study of Three Semi-Solid Extrusion 3D Printers", Pharmaceutics, vol. 12, No. 1239, published Dec. 19, 2020, 26 pages.
Search Report for FI Application No. 20216215 dated May 30, 2022, 1 page.
International Search Report for PCT/FI2022/050406 dated Apr. 4, 2023, 4 pages.
Written Opinion of the ISA for PCT/FI2022/050406 dated Apr. 4, 2023, 8 pages.

* cited by examiner

METHOD FOR PREPARING A VETERINARY MEDICAMENT DOSAGE WITH INKS AND A VETERINARY MEDICAMENT DOSAGE OBTAINABLE BY THE METHOD

CROSS-REFERENCE TO RELATED APPLICATIONS

This application is the U.S. national phase of International Application No. PCT/FI2022/050406 filed Jun. 13, 2022 which designated the U.S. and claims priority to FI patent application No. 20216215 filed Nov. 29, 2021, the entire contents of each of which are hereby incorporated by reference.

FIELD

The present invention relates to method to prepare medicines wherein the taste of the active pharmaceutical ingredient is masked. The invention relates also to medicament dose obtainable by the method.

BACKGROUND

It is well known that getting pets such as dogs and cats to take medicaments is difficult, challenging, and frustrating.

EP 1562549, EP 1996029, EP 2755498, U.S. Pat. No. 9,844,930, and WO2019199505 are aiming to solve the problem by providing medical product comprising an active pharmaceutical composition hidden in an edible composition of decent taste. A problem of this approach is that when the pet bites the medicament it may feel the unpleasant taste of the active pharmaceutical ingredient (API) in its mouth and then spit out the medicament.

An alternative approach, disclosed e.g., in U.S. Pat. No. 7,348,027 includes manufacture of veterinary formulation wherein the API is mixed with taste masking composition. However, the process disclosed therein is rather complicated including mixing together the API and the masking agent to form a mixture, subjecting the mixture to a first compression to form a slug, grinding the slug to particles, and subjecting the particles to form the final taste masked tablets.

Accordingly, there is still need for further methods for preparing veterinary medicaments.

SUMMARY

The following presents a simplified summary in order to provide a basic understanding of some aspects of various embodiments of the invention. The summary is not an extensive overview of the invention. It is neither intended to identify key nor critical elements of the invention, nor to delineate the scope of the invention. The following summary merely presents some concepts of the invention in a simplified form as a prelude to a more detailed description of exemplifying embodiments of the invention.

It was observed that when a veterinary medicament comprises repeating layers comprising one or more active pharmaceutical ingredients and layers comprising one or more taste masking agents, an edible dosage could be obtained.

Accordingly, it is an aspect of the present invention to provide a new method for preparing a veterinary medicament dosage using e.g., a 3D printer, the method comprising a) providing
- a printing substrate,
- at least a first ink comprising one or more taste masking agents,
- one or more further inks comprising one or more active pharmaceutical ingredients (API), b) printing on the printing substrate, using the at least first ink and the one or more further inks, plurality of layers so that each layer comprising the one or more APIs is surrounded by layers comprising one or more taste masking agents until required dose of the one or more APIs is obtained, provided that the dosage comprises at least two separate layers comprising the one or more APIs wherein API concentration of each layer comprising the one or more API is 0.1-1% by weight, and c) optionally recovering the veterinary medicament dosage from the printing substrate.

It is also an aspect of the present invention to provide a new a veterinary medicament dosage obtainable by the method of claim 1.

A number of exemplifying and non-limiting embodiments of the invention are described in accompanied dependent claims.

Various exemplifying and non-limiting embodiments of the invention and to methods of operation, together with additional objects and advantages thereof, are best understood from the following description of specific exemplifying embodiments when read in connection with the accompanying figures.

The verbs "to comprise" and "to include" are used in this document as open limitations that neither exclude nor require the existence of also unrecited features. The features recited in depending claims are mutually freely combinable unless otherwise explicitly stated. Furthermore, it is to be understood that the use of "a" or "an", i.e., a singular form, throughout this document does not exclude a plurality.

BRIEF DESCRIPTION OF FIGURES

The exemplifying and non-limiting embodiments of the invention are explained in greater detail below with reference to the accompanying figures, in which.

DESCRIPTION

The specific examples provided in the description given below should not be construed as limiting the scope and/or the applicability of the appended claims. Lists and groups of examples provided in the description given below are not exhaustive unless otherwise explicitly stated.

Figure 1:
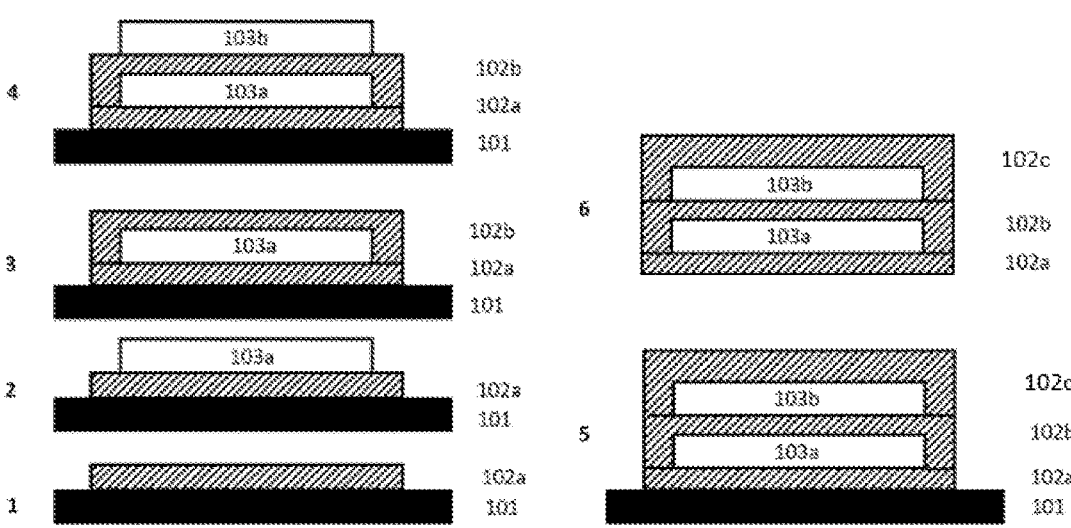
FIG. 1 shows an exemplary method according to a non-limiting embodiment of the present invention.

According to one embodiment the present invention concerns a method for preparation of a veterinary medicament dosage. An exemplary non-limiting embodiment of the method is shown in FIG. 1. The detailed printing and recovering steps are marked in the figure with numbers 1-6. Accordingly, the method comprises the following a) providing
- a printing substrate 101,
- at least a first ink comprising one or more taste masking agents, and
- a further ink comprising one or more active pharmaceutical ingredients (APIs).

b) printing:
1. Printing, using the first ink, a layer 102*a* comprising one or more taste masking agents on the printing substrate 101.
2. Printing, using the further ink a layer 103*a* comprising one or more APIs on the layer 102*a*,
3. Printing, using the first ink, a second layer 102*b* comprising the one or more taste masking agents on and around the layer 103*a*.
4. Printing, using the further ink a second layer 103*b* comprising the one or more APIs on the layer 102*b*.
5. Printing, using the first ink, a third layer 102*c* comprising the one or more taste masking agents on and around the layer 103*b*.

c) recovering
6. Recovering the veterinary dose from the printing substrate 101.

The recovering step of the method can be omitted if the printing is performed on an edible printing substrate. According to an exemplary embodiment the printing substrate is a package, such as a blister.

The printing, i.e., the layering is repeated until the required API dose in received.

The outermost layer should include one or more taste masking agents. The first ink does not include API, and the one or more further inks does not include taste masking agents.

Figure 2:
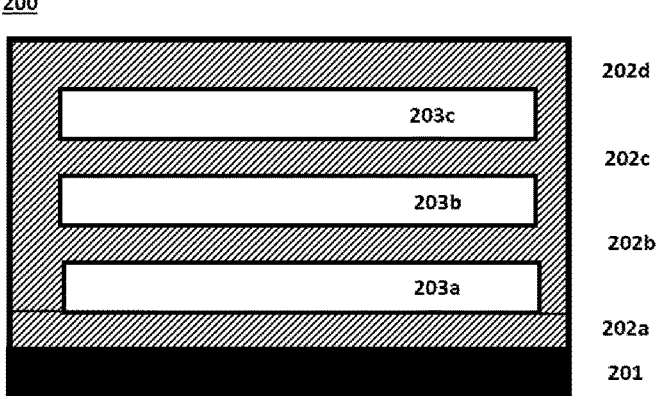
FIGS. 2 and 3 show exemplary section views of non-limiting drug dosages obtainable by the method of the present invention.

FIG. 2 shows a section view of an exemplary veterinary medicament dosage 200 obtainable by a method of the present invention. The dosage comprises an edible printing substrate 201, three separate layers 203*a-c* comprising one or more active pharmaceutical ingredients surrounded by layers 202*a-d* comprising one or more taste masking agents.

Printing of the layers can form any geometrical forms desired. Exemplary non-limiting geometric forms are circle, oval, and square. Also printing of free-form structures can be performed.

Figure 3:
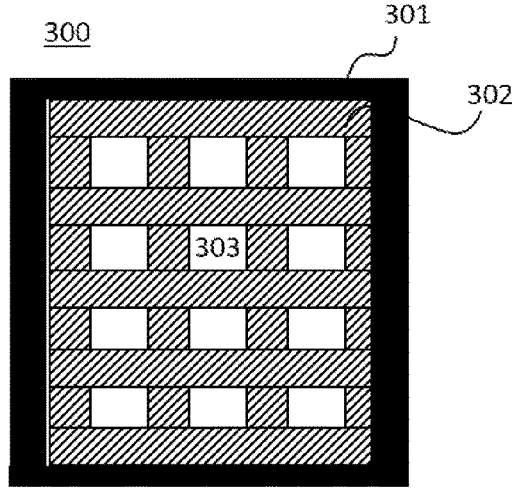

FIG. 3 shows an intersection of a top view of another exemplary dosage 300 obtainable by the method. The dosage comprises a printing substrate 301, layers comprising one or more taste masking agents as lattices 302, and layers comprising one or more APIs between the lattices. One of the API layers is marked with a reference sign 303. The outermost layers comprise a layer of the first ink. When the desired dosage from is printed, the dosage is recovered from the printing substrate 301 if needed.

The printing substrate can be chosen from materials that are able to host the printed compounds. Suitable printing substrate materials include cellulosic materials and other biodegradable materials, such as starch—and rice-based materials. In one embodiment, the printing substrate material is sugar-based decor paper or rice paper. In one embodiment, the substrate material is edible material. According to another embodiment recovering of the dosage includes removing the printing substrate. This is essential if the printing substrate is not edible.

According to a preferable embodiment the printing substrate material is any kind of orodispersible material or film. Exemplary orodispersible materials is a chitosan film or a hydroxypropyl methylcellulose film. In a further embodiment, the printing substrate material is a pharmaceutically acceptable material suitable to be administered orally or buccally. The printing substrate material is preferably recognized by the relevant authorities to be safe in medicinal applications. The substrate can contain also taste masking compounds which are deposited on the material by printing or by other techniques.

The one or more taste masking agents may be chosen according to target animal. An exemplary taste masking agents for dogs is artificial beef flavour. An exemplary taste masking agent for cats is artificial fish flavour. Further exemplary taste masking agents preferred by cats and dogs are bacon, lamb, chicken, poultry liver, beef, cheese, cod liver oil, marshmallow, molasses, and peanut butter. The masking agents should be printable. Accordingly, the masking agents are typically artificial flavours.

According to a preferable embodiment the printing substrate comprises one or mucoadhesive polymers. Mucoadhesiveness is an important property of the outermost layers since the dosage should stick to the mucosa and not float around in the mouth. A non-adhesive dosage is easier for an animal to spit out, leading to treatment failure. Mucoadhesive polymers have numerous hydrophilic groups, such as hydroxyl, carboxyl, amide, and sulphate. These groups attach to mucus or the cell membrane by various interactions such as hydrogen bonding and hydrophobic or electrostatic interactions. These hydrophilic groups also cause polymers to swell in water and, thus, expose the maximum number of adhesive sites. Exemplary mucoadhesive polymers are polyethylene glycol (PEG), polyvinyl alcohol (PVA) polyvinyl pyrrolidine (PVP), polyacrylic acid (PAA), poly hydroxyethyl methacrylate (PHEMA), chitosan, hydroxyethyl cellulose (HEC), hydroxypropyl cellulose (HPC), hydroxypropyl methylcellulose (HPMC), methylcellulose, gelatin, and sodium carboxymethyl cellulose (NaCMC).

According to a preferable embodiment the printing substrate is edible, and it comprises one or more taste masking ingredients and preferably also one or more mucoadhesive ingredients. According to this embodiment, the ink comprising one or more APIs can be printed directly on the printing substrate, and the printing substrate acts also as a layer comprising one of more taste masking agents.

The first ink used in the method of the present invention comprises one or more taste masking agents. The one or more taste masking ingredients may be chosen according to target animal. An exemplary taste masking ingredient for dogs is artificial beef flavour. An exemplary taste masking ingredient for cats is artificial fish flavour. Further exemplary taste masking agents preferred by cats and dogs are bacon, beef, cheese, cod liver oil, marshmallow, molasses, and peanut butter. Concentration of the one or more taste masking agents of the first ink is typically 0.5-5% by weight. An exemplary concentration is 1% by weight. The taste masking agents of the first ink may be same or different than those of the printing substrate. According to an embodiment the first ink does not include active pharmaceutical ingredient.

If the printing substrate is not edible, it is preferable that the first ink comprises the mucoadhesive polymers.

It is also possible to use more than one ink for producing layers comprising one or more taste masking agents.

The method of the present invention includes at least one further ink which comprises at least one API. An exemplary APIs are sildenafil, salbutamol, sotalol, atenolol, trilostane, prednisolone, phenobarbital, phenobarbital, libromide, gabapentin, and meloxicam.

The method produces a dosage comprising two or more separate layers comprising the API surrounded by layers comprising the one or more taste masking agents. Concentration of the API in ink is typically 0.1-5% by weight. An exemplary API concentration is 1% by weight. Another exemplary concentration is 0.5% by weight. Naturally, the API concentration can be higher if needed.

According to another embodiment method comprises use of at least one further ink comprising at least two APIs. According to this embodiment the method produces two or more separate layers comprising the APIs surrounded by layers comprising the one or more taste masking agents. Concentration of each API in the ink is typically 0.1-10% by weight. An exemplary API concentration is 1% by weight. Another exemplary concentration is 0.5% by weight. Naturally, the API concentration can be higher if needed.

According to still another embodiment the method comprises the use of at least two further inks, i.e., the second ink and the third ink, comprising a first API and a second API, respectively. An exemplary first API is a glucocorticoid prednisolone. An exemplary second API is meloxicam. According to this embodiment the method produces two or more API layers surrounded by layers comprising the one or more taste masking agents. Concentration of the APIs in the second and the third further ink is typically 0.1-5% by weight. An exemplary API concentration is 1% by weight. Another exemplary concentration is 0.5% by weight. Naturally, the API concentration can be higher if needed.

The inks used in the method comprise one or more polymers. Exemplary polymers are polyethylene glycol (PEG), polyvinyl alcohol (PVA) polyvinyl pyrrolidine (PVP), polyacrylic acid (PAA), poly hydroxyethyl methacrylate (PHEMA), chitosan, hydroxyethyl cellulose (HEC), hydroxypropyl cellulose (HPC), hydroxypropyl methylcellulose (HPMC), methylcellulose, gelatin, and sodium carboxymethyl cellulose (NaCMC). An exemplary polymer is HPC.

The API and the taste masking agents used in the inks are typically dissolved in a solvent having optimal properties for printability, such as surface tension and viscosity. According to one embodiment the API and the taste masking agents are dissolved in an aqueous solution or an organic solvent or mixtures thereof depending on their properties. In one embodiment, the API and the taste masking agents are dissolved in water. In another embodiment, API and the taste masking agents are dissolved in water/ethanol mixture. The API and the taste masking agents containing ink solution may also comprise edible mineral or vegetable oils and/or lipids, especially when fat-soluble ingredients are involved. The ink comprising API and the taste masking agents comprises optionally also viscosity modifiers and/or moisturizers, such as propylene glycol, glycerol, polyethylene glycol (PEG) and/or sodium carboxymethyl cellulose, for example. Also, surface-active agents, such as ethanol, isopropanol, and surfactants, may be used. In one embodiment, the solvent solution is propylene glycol/water mixture. In another embodiment, the solution is propylene glycol/water 30:70 mixture (vol-%). In one embodiment, the solution is a mixture of glycerol, ethanol, and water. In another embodiment, the solution is glycerol/ethanol/water 10:10:80 mixture (vol-%). Further, suspensions, colloidal or nano-particulate solutions and various formulation approaches, common for example in the pharmaceutical field, to enhance the properties of inherently poorly soluble substances can be used.

The method can use any 3D printing techniques known in the art. Exemplary printing methods include fused deposition modelling 3D printing, thermal inkjet printing, piezoelectric inkjet printing, and semi-solid extrusion printing. A preferable printing method is semi-solid extrusion printing since it does not require high temperatures. An exemplary process suitable for use in the method of the present invention has been described in Pharmaceutics 2020, 12, 1239 incorporated here by reference. Thickness of the layers is typically 0.01-2 mm.

According to another embodiment the present invention concerns a veterinary medicament dosage obtainable by a method shown above.

Advantages of the method of the present invention can be summarized as follows

The one or more APIs are distributed within the dosage and completely surrounded by layers comprising taste masking agents. Thus, biting the dosage does not give rise to sudden change of taste in a mouth.

Since the one or more APIs of the dosage can be divided between plurality of layers, API concentration of each layer can be low. This may be an essential property in particular with APIs of low solubility which are prone to crystallize.

The method allows s extemporaneous manufacturing of individually sophisticated dosages.

The method allows separate formulations that can be deposited in different sequences to mask the taste of the API or to make the taste attractive and to make the dosage to administration improved Dosage form can be shaped to help administration.

The specific examples provided in the description given above should not be construed as limiting the scope and/or the applicability of the appended claims.

What is claimed is:

1. A method for preparing a veterinary medicament dosage, the method comprising a) providing
   a printing substrate,
   at least a first ink comprising one or more taste masking agents,
   one or more further inks comprising one or more active pharmaceutical ingredients (API),
b) printing on the printing substrate, using the at least first ink and the one or more further inks, a plurality of layers so that each layer comprising the one or more APIs is surrounded by layers comprising one or more taste masking agents, wherein the dosage comprises at least two separate layers comprising the one or more APIs, wherein the API concentration of each layer comprising the one or more API is 0.1-1% by weight, and
c) optionally recovering the veterinary medicament dosage from the printing substrate.

2. The method according to claim 1, wherein the at least first ink does not comprise one or more APIs.

3. The method according to claim 1, wherein the printing substrate comprises orodispersible material.

4. The method according to claim 1, wherein the printing substrate comprises one or more mucoadhesive polymers.

5. The method according to claim 1, wherein the first ink comprises one or more mucoadhesive polymers.

6. The method according to claim 1, wherein at least one of the one or more further inks comprises one or more mucoadhesive polymers.

7. The method according to claim 4, wherein the mucoadhesive polymer is selected from a group consisting of polyethylene glycol (PEG), polyvinyl alcohol (PVA) polyvinyl pyrrolidine (PVP), polyacrylic acid (PAA), poly hydroxyethyl methacrylate (PHEMA), chitosan, hydroxyethyl cellulose (HEC), hydroxypropyl cellulose (HPC), hydroxypropyl methylcellulose (HPMC), methylcellulose, gelatin, and sodium carboxymethyl cellulose (NaCMC).

8. The method according to claim 1, wherein the printing substrate comprises one or more taste masking agents.

9. The method according to claim 1, wherein the one or more taste masking agents are selected from a group consisting of artificial bacon flavor, artificial beef flavor, artificial cheese flavor, cod liver oil, artificial marshmallow flavor, artificial molasses flavor, and artificial peanut butter flavor.

10. The method according to claim 1, wherein the one or more active pharmaceutical ingredients are selected from a group consisting of sildenafil, salbutamol, sotalol, atenolol, trilostane, prednisolone, phenobarbital, potassium bromide, gabapentin, and meloxicam.

11. The method according to claim 1, wherein the thickness of each layer comprising the one or more APIs is 0.01-2 mm.

12. The method according to claim 1, wherein the thickness of each layer comprising the one or more taste masking agents is 0.01-2 mm.

13. The method according to claim 1, wherein the printing is semi-solid extrusion 3D printing.

14. A veterinary medicament dosage obtainable by the method according to claim 1.

15. The method according to claim 2, wherein the printing in step b is performed so that each layer comprising the one or more APIs is completely surrounded by layers comprising one or more taste masking agents.

\* \* \* \* \*